(12) United States Patent
Sharpe et al.

(10) Patent No.: US 9,358,092 B2
(45) Date of Patent: *Jun. 7, 2016

(54) POLYMERIC MEMBERS AND METHODS FOR MARKING POLYMERIC MEMBERS

(75) Inventors: Johnathan Charles Sharpe, Hamilton (NZ); Thomas B. Gilligan, College Station, TX (US); Richard W. Lenz, Eastman, WI (US); Juan F. Moreno, College Station, TX (US)

(73) Assignee: Inguran, LLC, Navasota, TX (US)

( * ) Notice: Subject to any disclaimer, the term of this patent is extended or adjusted under 35 U.S.C. 154(b) by 55 days.

This patent is subject to a terminal disclaimer.

(21) Appl. No.: 14/110,117

(22) PCT Filed: Apr. 17, 2012

(86) PCT No.: PCT/US2012/033920
§ 371 (c)(1),
(2), (4) Date: Oct. 4, 2013

(87) PCT Pub. No.: WO2012/145306
PCT Pub. Date: Oct. 26, 2012

(65) Prior Publication Data
US 2014/0023813 A1 Jan. 23, 2014

Related U.S. Application Data

(60) Provisional application No. 61/476,751, filed on Apr. 18, 2011, provisional application No. 61/483,490, filed on May 6, 2011.

(51) Int. Cl.
| G03C 1/73 | (2006.01) |
| A61D 19/04 | (2006.01) |
| B41J 2/44 | (2006.01) |
| B23K 26/00 | (2014.01) |

(Continued)

(52) U.S. Cl.
CPC .......... *A61D 19/024* (2013.01); *A01N 1/0268* (2013.01); *B23K 26/0036* (2013.01); *B23K 26/0084* (2013.01); *B23K 26/0807* (2013.01);

(Continued)

(58) Field of Classification Search
None
See application file for complete search history.

(56) References Cited

U.S. PATENT DOCUMENTS

| 3,507,281 A | 4/1970 | Cassou |
| 3,877,430 A | 4/1975 | Wieder |

(Continued)

FOREIGN PATENT DOCUMENTS

| CN | 101595171 A | 12/2009 |
| DE | 19849543 A1 | 4/1999 |

(Continued)

OTHER PUBLICATIONS

Holtz et al. "laser induced ablation of polymers using a patterned dopant generated form a leuco-dye precursopr via flood exposure: a 'portable conformable mask' approach to laser ablation of PMMA at 351 nm", Appl. Phys. A, vol. 60 pp. 529-535 (1985).*

(Continued)

*Primary Examiner* — Martin Angebranndt
(74) *Attorney, Agent, or Firm* — Ryan Christensen; Hashim Rahman

(57) ABSTRACT

Generally, polymeric members and laser marking methods for producing visible marks on polymeric members, such as on thin and/or curved surfaces. The laser marking methods can include methods of laser marking straws with the step of matching laser source properties to the properties of straws being marked or with the step of laser marking straws having photochromic dyes.

10 Claims, 8 Drawing Sheets

(51) Int. Cl.
| | |
|---|---|
| *B23K 26/08* | (2014.01) |
| *A61D 19/02* | (2006.01) |
| *B29C 59/16* | (2006.01) |
| *G03C 5/56* | (2006.01) |
| *C12M 1/24* | (2006.01) |
| *B41M 5/26* | (2006.01) |
| *A01N 1/02* | (2006.01) |
| *B23K 26/18* | (2006.01) |
| *B23K 26/36* | (2014.01) |
| *B23K 26/40* | (2014.01) |

(52) U.S. Cl.
CPC ............... *B23K 26/18* (2013.01); *B23K 26/362* (2013.01); *B23K 26/40* (2013.01); *B29C 59/165* (2013.01); *B41J 2/442* (2013.01); *C12M 1/24* (2013.01); *G03C 1/733* (2013.01); *G03C 5/56* (2013.01); *B23K 2201/007* (2013.01); *B23K 2203/42* (2015.10); *B41M 5/267* (2013.01); *Y10T 428/139* (2015.01)

(56) References Cited

U.S. PATENT DOCUMENTS

| | | | |
|---|---|---|---|
| 4,990,792 A | 2/1991 | Frei | |
| 4,992,347 A | 2/1991 | Hawkins et al. | |
| 5,111,523 A | 5/1992 | Ferlier et al. | |
| 5,160,940 A | 11/1992 | Cassou et al. | |
| 5,289,767 A | 3/1994 | Montalto et al. | |
| 5,444,466 A | 8/1995 | Smyczek et al. | |
| 5,508,499 A | 4/1996 | Ferrario | |
| 5,558,449 A | 9/1996 | Morgavi | |
| 5,559,231 A | 9/1996 | Yamamoto et al. | |
| 5,560,845 A | 10/1996 | Birmingham et al. | |
| 5,671,667 A | 9/1997 | Simmet | |
| 6,303,673 B1 | 10/2001 | Clarke et al. | |
| 6,386,458 B1 | 5/2002 | Leiber et al. | |
| 7,824,748 B2 | 11/2010 | Dalvey et al. | |
| 7,995,196 B1* | 8/2011 | Fraser ............... G06K 9/00577 356/71 |
| 8,196,807 B2 | 6/2012 | Grimard | |
| 2001/0036537 A1 | 11/2001 | Jux et al. | |
| 2002/0067900 A1 | 6/2002 | Mills et al. | |
| 2003/0008234 A1 | 1/2003 | Berneth et al. | |
| 2003/0157475 A1 | 8/2003 | Schenk | |
| 2003/0174990 A1 | 9/2003 | Andrieu et al. | |
| 2004/0043308 A1 | 3/2004 | Lutz et al. | |
| 2005/0080358 A1 | 4/2005 | Iwami et al. | |
| 2005/0116046 A1 | 6/2005 | Borgsmueller et al. | |
| 2005/0218126 A1 | 10/2005 | Leyvraz | |
| 2006/0016543 A9 | 1/2006 | Majumdar et al. | |
| 2006/0057555 A1 | 3/2006 | Damari et al. | |
| 2006/0068315 A1 | 3/2006 | Gore | |
| 2006/0072444 A1 | 4/2006 | Engel et al. | |
| 2007/0113358 A1 | 5/2007 | Rabolt et al. | |
| 2007/0235414 A1 | 10/2007 | Shah et al. | |
| 2007/0269740 A1 | 11/2007 | Blank et al. | |
| 2008/0164873 A1 | 7/2008 | Hoekstra et al. | |
| 2008/0179301 A1 | 7/2008 | Garty et al. | |
| 2008/0194719 A1 | 8/2008 | Duan et al. | |
| 2009/0093054 A1 | 4/2009 | Sjogren et al. | |
| 2009/0123992 A1 | 5/2009 | Chin | |
| 2009/0162531 A1 | 6/2009 | Nesbitt | |
| 2009/0181156 A1 | 7/2009 | Nesbitt | |
| 2009/0266804 A1 | 10/2009 | Costin et al. | |
| 2010/0015558 A1 | 1/2010 | Jarvis et al. | |
| 2010/0025387 A1 | 2/2010 | Arai et al. | |
| 2010/0141729 A1 | 6/2010 | Petsch et al. | |
| 2010/0198620 A1 | 8/2010 | Mullenger et al. | |
| 2011/0076712 A1 | 3/2011 | Gilligan et al. | |
| 2011/0130657 A1* | 6/2011 | Chomas et al. ............... 600/433 |
| 2011/0239791 A1 | 10/2011 | Fici | |
| 2012/0021362 A1 | 1/2012 | Jarvis et al. | |
| 2012/0089490 A1 | 4/2012 | Blaine | |
| 2012/0263863 A1 | 10/2012 | Nesbitt | |
| 2012/0264207 A1* | 10/2012 | Sharpe et al. ............... 435/307.1 |
| 2014/0046126 A1* | 2/2014 | Gilligan et al. ................ 600/35 |

FOREIGN PATENT DOCUMENTS

| | | |
|---|---|---|
| DE | 29816802 U1 | 2/2000 |
| EP | 0798118 B1 | 3/2002 |
| JP | 2004-321395 | * 11/2004 |
| JP | 2004-321395 A | 11/2004 |
| WO | 2004101870 A2 | 11/2004 |
| WO | 2005109332 A1 | 11/2005 |
| WO | 2006018640 A1 | 2/2006 |
| WO | 2010023102 A1 | 3/2010 |
| WO | 2011012397 A1 | 2/2011 |

OTHER PUBLICATIONS

US Notice of Allowance dated Aug. 19, 2014, issued in related U.S. Appl. No. 13/448,948 (8 pp).
US Office Action dated Dec. 13, 2013, issued in related U.S. Appl. No. 13/448,948 (11 pp).
US Final Office Action dated Oct. 22, 2013, issued in related U.S. Appl. No. 13/448,948 (11 pp).
Synrad, Inc., "Featured application: Laser marking curved or cylindrical surfaces", Newsletter Issue 243, Aug. 2010, 3pp.
Synrad, Inc., "Marking PVC tubing", Newsletter Issue 72, Oct. 2003, 3pp.
Synrad, Inc., "Contrasting marks in PVC" and "marking electrical connectors", Newsletter Issue 81, (first page) 3pp.
Synrad, Inc., "Marking polyethylene dip tubes", Newsletter Issue 116, Jul. 2005, 3pp.
Synrad, Inc., "Marking common plastics", Newsletter Issue 86, Apr. 2004, 3pp.
Hofmann, et al., High contrast and intact surface—a challenge in laser marking of plastics, Proc. SPIE, vol. 774, 1987, pp. 156-180.
Benifla, Jean-Louis, et al., "Safety of cryopreservation straws for human gametes or embryos: a preliminary study with human immunodeficiency virus-1", Hum. Reprod. (2005) 15 (10): 2186-2189.
Chinese office action for application No. 201280018875.3 issued on Oct. 30, 2014.
Synrad, Inc., "Contrasting marks in PVC" and "marking electrical connectors", Newsletter Issue 81, 3pp. Feb. 19, 2004.
U.S. Office Action dated Mar. 6, 2014, issued in related U.S. Appl. No. 13/448,948 (16 pp).
U.S. Office Action dated May 29, 2014, issued in related U.S. Appl. No. 13/448,948 (15 pp).
PCT International Search Report and Written Opinion dated Aug. 3, 2012 issued in corresponding PCT Application No. PCT/US2012/033920 (20 pages).
US Office Action dated Jul. 24, 2013 issued in corresponding U.S. Appl. No. 13/448,948 (9 pages).
Marshall, Clif; "Integrated Field Data Transfer Using Bar Coded Semen Straws"; Symposium, 2008, pp. 17-23; Proceedings of the 22nd Technical Conference on Artificial Insemination & Reproduction (7 pages).
"Animal Reproduction Technology—Bovine"; Minitube; 2010 (44 pages).
US Office Action dated Sep. 10, 2015 for U.S. Appl. No. 14/057,743.
EP Examination Report dated Oct. 27, 2015 for U.S. Appl. No. 12774883.8.
US Final Office Action dated Dec. 24, 2015 for U.S. Appl. No. 14/057,743.
AU Examination Report dated Dec. 9, 2015 for AU Application No. 2013331042.
CN Office Action dated Dec. 7, 2015 for US Application No. 201280018875.3.
Chinese Office Action Issued on Jun. 25, 2015 in related CN Application No. 201280018875.3.
Canadian Examiner's Requisition dated Mar. 17, 2016 for CA Application No. 2,833,172.
Canadian Examiner's Requisition dated Apr. 4, 2016 for CA Application No. 2,888,458.
US Notice of Allowance dated Feb. 5, 2016 for U.S. Appl. No. 14/057,743.

* cited by examiner

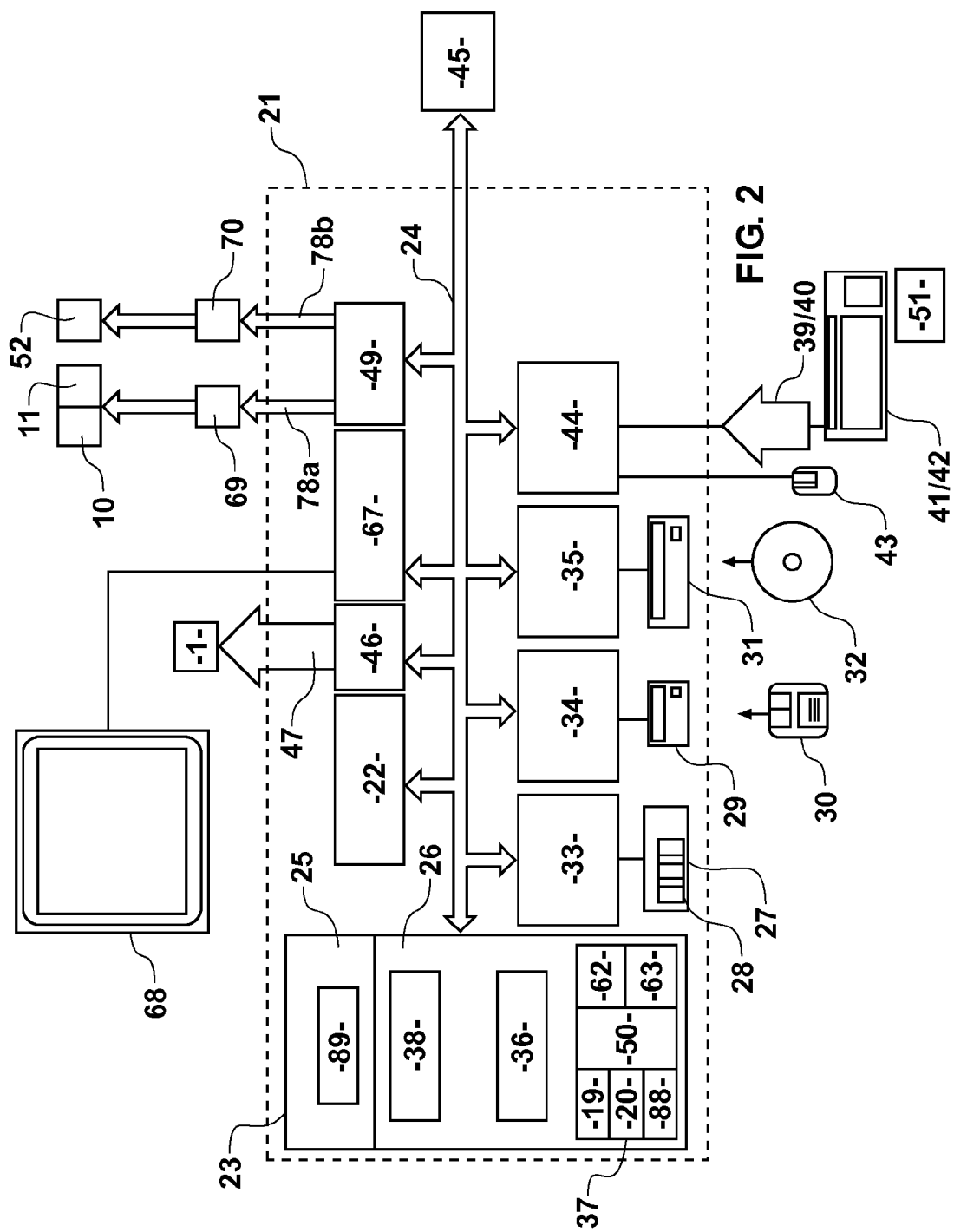

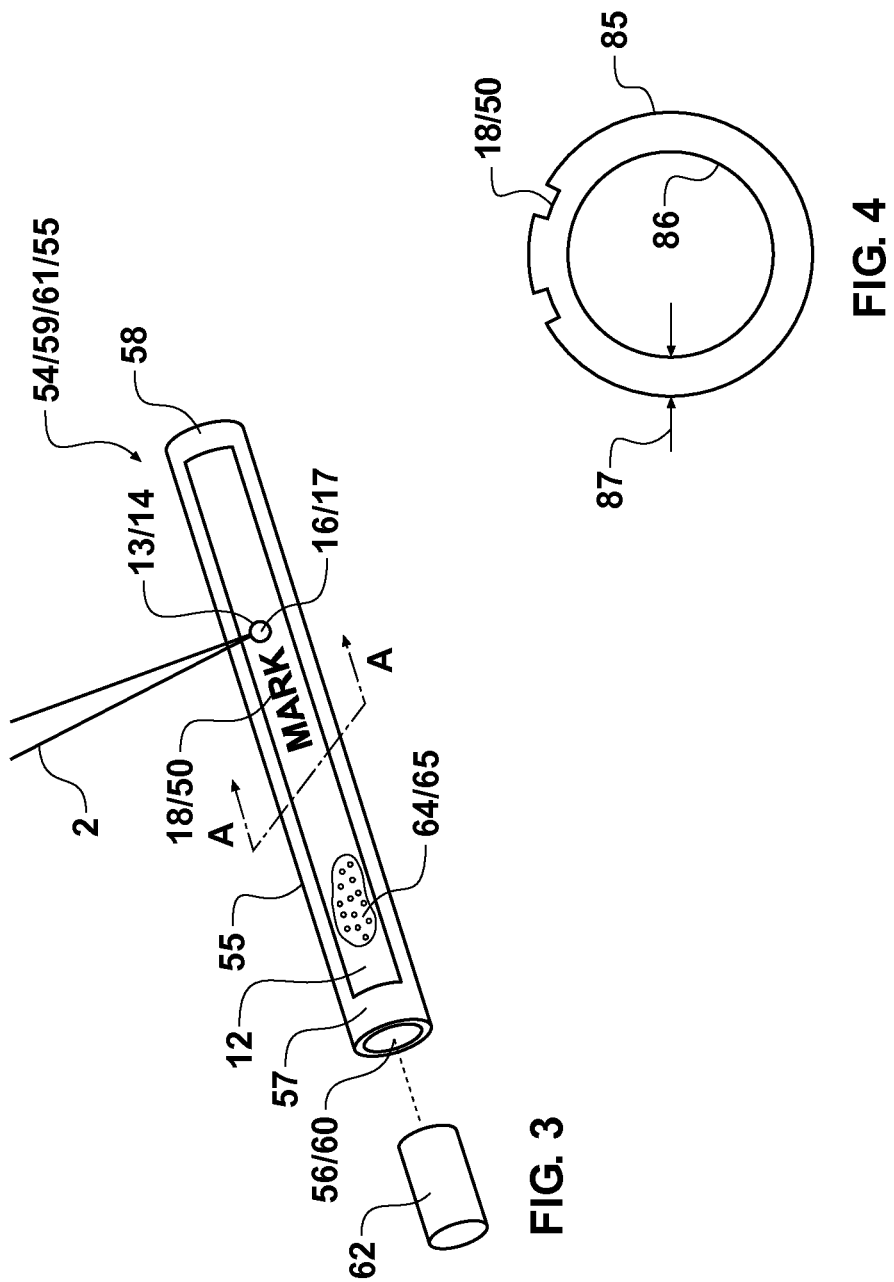

POLYMERIC MEMBERS AND METHODS FOR MARKING POLYMERIC MEMBERS

This application is a national stage entry of International Application No. PCT/US2012/033920, filed Apr. 17, 2012, which itself claims priority to U.S. Provisional Patent Application No. 61/476,751, filed Apr. 18, 2011, and U.S. Provisional Patent Application No. 61/483,490, filed May 6, 2011 the entire contents of which are incorporated herein by reference.

FIELD OF INVENTION

The present invention generally relates to polymeric members and laser marking methods for producing visible marks on polymeric members, and more particularly relates to laser marked straws used for containing biological materials and methods for generating visible marks on straws with a laser.

BACKGROUND

Straws, such as 0.25 ml straws and 0.5 ml straws, may be used to transport and store biological products, biological materials, biological fluids, embryos, inseminate for the artificial insemination of an animal, semen, ova, or the like and may be cooled or super cooled for storage. Marking individual straws is often desirable for identifying the type of cells contained and their source.

Conventionally, straws may be serially processed through a printer prior to introduction of contents for storage. Straws are typically of very narrow diameter, ranging from 2 millimeters ("mm") to 5 mm, and usually about 133 mm or about 280 mm long. Hence, the area on the external surface on which marks may be imprinted can be limited. The task of printing on straws may be unsuited for most types of impact printing, not only because of the non-planar surfaces to be imprinted, but also because the empty or fluid-filled plastic straws may yield or deform if subjected to localized pressure. Currently, printing on conventional cylindrical artificial insemination straws typically involves a mechanical system that accepts individual straws from a hopper containing a plurality of straws, and passes the straws length wise proximate the printer head of a stationary ink-jet printer. The printer head disperses ink droplets at appropriate volumes, trajectories and times to produce marks on one side along the length of the straw. This approach can produce visible marks with respect to the background color of the straw to assist in identification of the content of each straw. Marks typically applied to the straws which, for example, contain inseminates for artificial insemination provide characters which can identify the source of the semen, animal name, date, company information, freeze lot, and sex-selection characteristics such as being enriched for X-chromosome bearing sperm or Y chromosome bearing sperm, or the like.

However, there are substantial unresolved problems associated with marking straws with an ink-jet printer and with the resulting ink marks. One substantial problem with marking straws by ink-jet printer is that characters may not be sufficiently small and of sufficiently resolved to include all the necessary or desired information on the imprintable area of the straw. This problem may be exacerbated due to international trade requirements which now necessitate additional information on individual straws. Additionally, the current resolution and accuracy of ink-jet printing limits the complexity of the characters that can be printed on the straw and may not be suitable to print 1D, 2D, 3D or grayscale barcodes, logos, trademarks, or the like. Additionally, small variations in the speed at which straws pass the ink-jet printer head can result in mark distortions such as compressed, stretched, or variable contrast marks.

Another substantial problem with marking straws by ink-jet printer can be that ink jet printing is a once over process which precludes imprinting one straw multiple times. Conventional straw imprinters do not control straw orientation (rotation/roll) with respect to ink jet print head. Thus, straws cannot be preprinted with information constant between straws, such as company information, production location, trademarks, logos, or the like, and then reprinted at a subsequent date with information variable between straws such as bull code, lot number, date, or the like.

Another substantial problem with marking straws by an ink-jet printer can be that the imprinted information may not be permanent. Ink jet printer ink may be soluble in a variety of solvents commonly used in production of straws containing biological products such as methyl alcohol, ethyl alcohol, acetone, ether, or the like. Accordingly, information imprinted in ink jet printer ink can be readily removed by contact with such solvents. Similarly, information imprinted in ink jet printer ink can be removed by slight abrasion.

Another substantial problem with marking straws by ink-jet printer can be that consumables such as the ink-jet printer ink and thinner used to clean the ink jet printer may have a level of toxicity, can be spilled and time consuming to clean up, and can be expensive.

Another substantial problem with impact marking or ink-jet printer marking can be the relative ease in counterfeiting the marks by non-certified manufacturers. Conventional marking is relatively large and uncomplicated and does not include authenticity markings.

Another substantial problem with impact marking or ink jet printer marking can be the lack of raised surfaces. Accordingly, the marks cannot be interpreted by touch.

A wide variety of polymeric materials can be laser marked such as liquid crystal polymer (LCP), polyethersulfone (PES), polyphenalsulfide (PES), polystyrene, polypropylene, polyethylene, polyethylene terephthalate (PET), polyvinylchloride (PVC) and acrylonitrile butadiene styrene (ABS). However, laser beam induced marking of certain configurations of polymeric members such as straws having an axial body defining an axial passage communicating between a pair of body ends continue to be marked by use of ink jet printers with ink-jet ink as above-described. In particular, straws used for the storage of biological materials such as sex sorted sperm, conventional semen, eggs, cells, embryos and similar cellular materials continue to be ink-jet printed.

Prior attempts to render a mark on such polymeric members by incidence of a laser beam resulted in marks which were too faint or resulted in brittleness, shrinkage, bowing, warping, or the like which made the polymeric member subsequently unsuitable for deposit of the biological material, filling with biological liquids, cryogenic freezing of the polymeric member containing the biologic material, storing, or handling.

The polymeric members and laser marking methods described herein address each of these substantial problems of the conventional straw marking.

SUMMARY OF INVENTION

Accordingly, a broad object of the invention can be to provide a straw laser marking method for marking the curved, thin surface of a straw, such as a cryopreservation straw. The laser beam may be optically focused to establish a laser beam spot of fixed dimensional boundary and adjustable fluence on each of a plurality of pixels located on the marking plane for an irradiation dwell period sufficient to produce a mark.

Another broad object of the invention can be to provide methods of straw laser marking including adjusting laser beam characteristics within marking value ranges which allow visible marking of a variety of polymeric matrices of straws without straw deformation.

Still another broad object of the invention can be to provide methods of straw laser marking including adjusting laser beam characteristics within marking value ranges which allow visible marking of a variety of polymeric matrices of straws without creating straw permeability to biological materials including, without limitation, pathogens such as bacteria and viruses.

Yet another broad object of the invention can be to provide a plurality of laser beam characteristics matched to a corresponding plurality of marking value ranges which allow a laser beam directed incident upon the marking plane of any one of a variety of straws differentiated by dispersed colorant, or dye, with the corresponding polymeric matrices to be visibly marked.

Another broad object of the invention can be to provide methods of straw laser marking which include matching laser beam characteristics to straw characteristics for reducing power and time requirements for marking straws.

Still another broad object of the invention can be to provide a straw having a thickness of between about 0.1 mm and about 0.2 mm with visible laser etched markings. Such a straw may retain an unwarped shape and remain impermeable providing a suitable container for cryopreserving biological materials.

Another broad object of the invention can be to provide methods of straw laser marking which includes matching laser beam characteristics to straw characteristics, whereby the straw characteristics may be modified for marking.

Yet another broad object of the invention can be to provide methods for marking a straw with a laser which provides increased protection to ultra violet light.

Still another object of the invention can be to improve the properties of straws for marking with the inclusion of photochromic dyes that may selectively alter straw characteristics.

Naturally, further objects of the invention are disclosed throughout other areas of the specification, drawings and claims.

BRIEF DESCRIPTION OF THE DRAWINGS

FIG. 2 illustrates a diagram of particular computer means and control module means of embodiments described herein.

FIG. 3 illustrates a perspective view of a polymeric member laser marked in accordance with particular embodiments described herein.

FIG. 4 illustrates a cross sectional view of a polymeric member laser marked in accordance with particular embodiments described herein.

DETAILED DESCRIPTION

Figure 1:
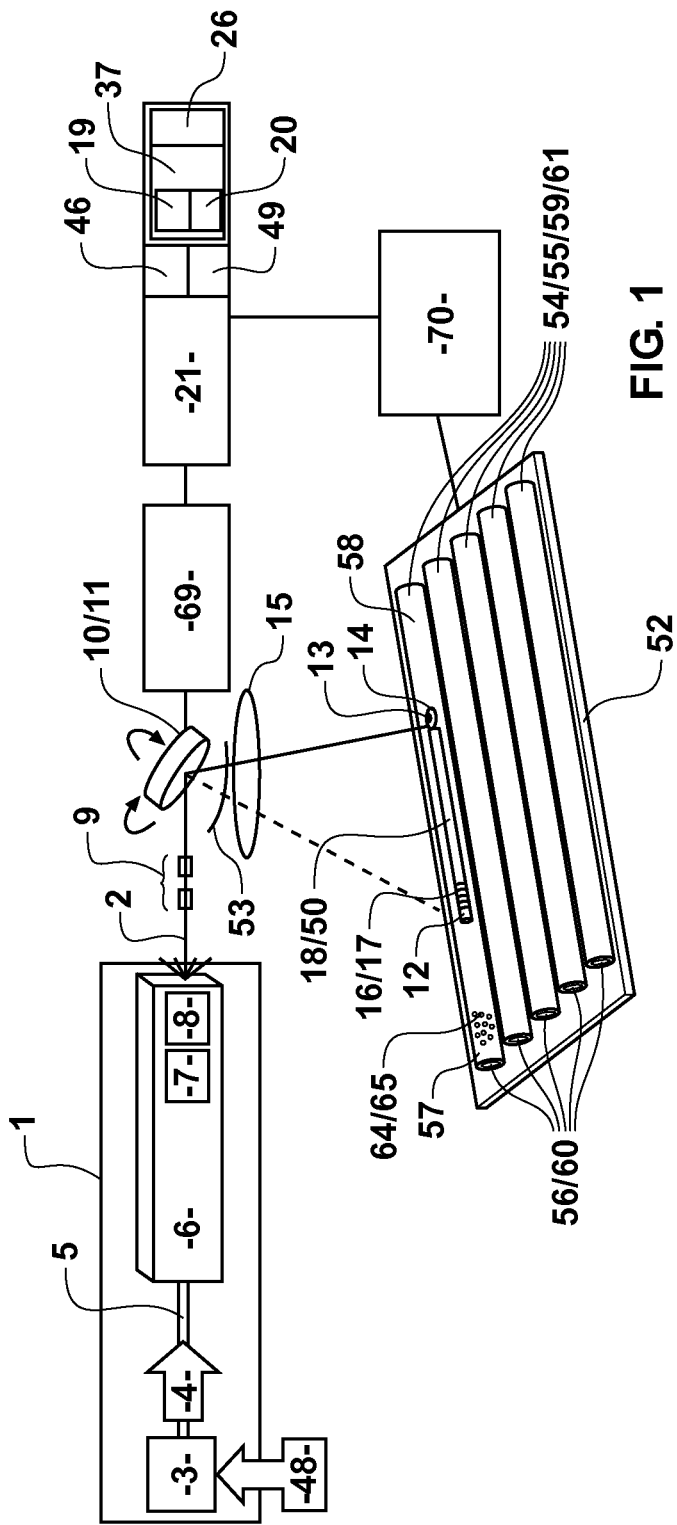
FIG. 1 illustrates a diagram relating to embodiments described herein.

Now referring primarily to FIG. 1, a laser source (1) that operates to generate a laser beam (2) is illustrated. A non-limiting example of a laser source (1) may include a laser diode (3) which generates laser light (4) that travels within a fiber optic cable (5) to a laser head (6). At a fixed voltage, amperage (48) to the laser diode (3) may be adjusted to provide a laser beam (2) adjustably variable within a power range. The laser head (6) may contain a laser crystal (7) and a Q-switch (8). As a non-limiting example, the laser crystal (7) may be a vanadate (Nd:YVO4) laser crystal (7) which absorbs laser light (4) at 808 nanometers ("nm") from the laser diode (3) and produces a continuous waveform laser light (4) at a wavelength of 1064 nm. The Q-switch (8) acts to convert the continuous waveform laser light (4) from the laser crystal (7) (such as the vanadate crystal) to serial laser beam pulse(s) (9). The Q-switch (8) may be opened and closed in the range of about 1,000 to about 70,000 times per second. While the Q-switch (8) is open, the stored energy of the laser crystal (7) emits a laser beam (2) until the Q-switch (8) closes resulting in a laser beam pulse (9). The duration of the laser beam pulse (9) may be adjusted by a change in the switch rate of the Q-switch (8). It is not intended that the above example of a laser source (1) be limiting with respect to the numerous and wide variety of laser sources (1) which may be utilized to produce a laser beam (2) (whether continuous or pulsed) having a correspondingly wide range of waveform characteristics such as frequency or amplitude or both that may be suitable for use with particular embodiments described herein. In particular, non-limiting examples of suitable laser sources (1) include Nd:YVO or YAG lasers (wavelength 1064 nm), frequency-doubled Nd:YVO or YAG lasers (wavelength 532 nm) and Excimer lasers (wavelength 193 nm 351 nm).

The laser beam (2) emitted from the laser head (6), whether continuous or pulsed, may be received by one or a pair of scanning mirrors (10)(11), which may be collectively referred to as a steering element. The pair of scanning mirrors (10)(11) can be positioned to direct the laser beam (2) or each of the laser beam pulses (9) incident upon a marking plane (12). Alternatively, acousto-optical modulators and other refractive and reflective elements could be used to steer the laser beam (2). The laser beam (2) may also be optically focused to produce a laser beam spot (13) having a boundary (14) of fixed dimension on the marking plane (12) by passing the laser beam (2), or each of the laser beam pulses (9), through a focusing lens (15), such as an F-Theta lens. By optically focusing the laser beam (2) through the focusing lens (15) the boundary (14) of the laser beam spot (13) can be adjusted to a diameter in the range of about 20 microns to about 100 microns. Particular embodiments provide a laser beam spot (13) incident upon the marking plane (12) with a diameter of about 40 microns. If the power of the laser beam (2) is fixed, the lesser the dimension of the laser beam spot (13) the greater the fluence (62) of each of the laser beam pulses (9) incident upon the marking plane (12).

A plurality of pixels (16) may each be assigned to a corresponding plurality of pixel locations (17) in relation to the marking plane (12). The plurality of pixel locations (17) may correspond to a marking pattern (50) containing information in the form or text, barcodes, logos, trademarks, or other representations of information. The laser beam spot (13) may be centered over one or more of the plurality of pixels (16) by operation of the pair of scanning mirrors (10)(11). The step size (88), or spacing between the plurality of pixels (16), can be adjusted to increase or decrease the distance between any two of the plurality of pixel locations (17). If, for example, the laser beam spot (13) has a diameter of about 40 microns and the distance between any two of the plurality of pixels (16) is about 30 microns, serial centered incidence of the laser beam (2) on any two of the plurality of pixels (16) will result in overlapping incidence of the laser beam (2) on the marking plane (12). If the laser beam spot (13) has a diameter of about 40 microns and the distance between any two of the pixel locations (17) is about 50 microns, then serial centered incidence of the laser beam (2) on any two of the plurality of pixels (16) will result in spaced incidence of the laser beam (2) on the marking plane (12). Understandably, a lesser diameter laser beam spot (13) and a lesser distance between the plurality of pixel locations (17) can increase the resolution of a resulting visible mark (18) on the marking plane (12), but can also increase the marking period (19) in which to complete marking of the visible mark (18).

As to each of the plurality of pixel locations (17) an irradiation dwell period (20) can be adjusted to increase or decrease the amount of time the laser beam (2) dwells at each of the plurality of pixel locations (17). As a non-limiting example, a relatively low fluence (62) of the laser beam (2) may necessitate a longer irradiation dwell period (20) at each of the plurality of pixel locations (17) to achieve the same result as compared to a relatively high fluence (62) at each of the same plurality of pixel locations (17) acting on the same marking plane (12). The irradiation dwell period (20) may also be adjusted to encompass the duration of one laser beam pulse (9) or the duration of a plurality of laser beam pulses (9) at the same one of the plurality of pixel locations (17).

The term visible, may be interpreted as visible by the naked eye, as well as by machine vision approaches, since at some stage the straws may be 'read' by a device that is computer-based or has aspects of artificial intelligence that mimic human functions. Similarly, the term visible markings (18) may include laser etched markings, such as divots, wells, charring, or other localized modifications of the surface depth or color of the surface being marked which are visible to the naked eye or to machine vision approaches.

Producing visible markings (18) in a desired marking pattern (50) requires coordination of a variety of factors. One or more than one laser source (1), may produce laser beam pulses (9) at a coordinated rate, if pulsed, and may have a coordinated fluence (62) incident upon the marking plane (12) that can be adjusted by varying laser beam power and/or boundary (14) of the laser beam spot (13). The positioning of the pair of scanning mirrors (10)(11), or alternatively beam light positioners, to direct the laser beam (2) incident upon the marking plane (12) may be coordinated to control spacing between a plurality of pixel locations (17), as well as the irradiation dwell period (20) of the laser beam (2) incident upon each of the plurality of pixels (16). The scanning mirrors (10)(11), or another laser beam positioning mechanism, may be replaced by, or used in conjunction with a carrier (52) movable relative to the laser beam (2). For example, the carrier (52) may be coordinated with a carrier position controller (70) for movement in the longitudinal direction, while the scanning mirrors (10)(11) can direct the laser beam (2) orthogonally.

Now referring primarily to FIGS. 1 and 2, coordination of the above-described factors can be controlled by a computer (21) having a processing unit (22), a memory element (23), and a bus (24) which operably couples components of the computer (21), including without limitation the memory element (23) to the processing unit (22). The computer (21) may be a conventional computer (21) such as a personal computer or a lap top computer; however the invention is not so limited. The processing unit (22) may comprise one central-processing unit (CPU), or a plurality of processing units which operate in parallel to process digital information. The bus (24) may be any of several types of bus configurations including a memory bus or memory controller, a peripheral bus, and a local bus using any of a variety of bus architectures. The memory element (23) may, without limitation, be a read only memory (ROM) (25) or a random access memory (RAM) (26), or both. A basic input/output system (89), containing routines that assist transfer of data between the components of the computer (21), such as during start-up, may be stored in ROM (25). The computer (21) may further include a hard disk drive (27) for reading from and writing to a hard disk (28), a magnetic disk drive (29) for reading from or writing to a removable magnetic disk (30), and an optical disk drive (31) for reading from or writing to a removable optical disk (32) such as a CD ROM or other optical media.

The hard disk drive (27), magnetic disk drive (29), and optical disk drive (31) are connected to the bus (24) by a hard disk drive interface (33), a magnetic disk drive interface (34), and an optical disk drive interface (35), respectively. The drives and their associated computer-readable media provide nonvolatile storage of computer-readable instructions, data structures, program modules and other data for the computer. It may be appreciated by those skilled in the art that any type of computer-readable media that can store data that is accessible by the computer (21), such as magnetic cassettes, flash memory cards, digital video disks, Bernoulli cartridges, random access memories (RAMs), read only memories (ROMs), and the like, may be used in a variety of operating environments.

One or more laser control modules (36) or marking modules (37) and an operating system (38) (hard wired circuitry may be used in place of, or in combination with, software instructions) may be stored on the hard disk (28), magnetic disk (30), optical disk (32), ROM (25), or RAM (26), which may be served by the computer server. A computer user (51) may enter marking commands (39) and marking data (40) into the computer (21) through input devices (41), such as a keyboard (42) and a pointing device (43) such as a mouse although other input devices (41) can be used such as touch screen, joy stick, or the like. These and other input devices (41) are often connected to the processing unit (22) through a serial port interface (44) that can be coupled to the bus (24), but may be connected by other interfaces, such as a parallel port, game port, or a universal serial bus (USB). A monitor (68) or other type of display device may also be connected to the bus (24) via a monitor interface (67), such as a video adapter, or the like. In addition to the monitor (68), the computer (21) may further include other peripheral output devices (45), such as speakers and printers.

The laser control modules (36) provide a sequence of instructions executed by the processing unit (22). Execution of the instructions by the processing unit (22) causes a laser control unit (46) to perform steps to generate laser control signals (47) for operation of the laser source (1) including the laser diode (3), amperage (48) to the laser diode (3) and any switch such as the Q-switch (8) to generate laser beam pulses (9).

The marking modules (37) provide a sequence of instructions executed by the processing unit (22). Execution of the instructions by the processing unit (22) causes the marking control unit (49) to mark, in serial order, each of a plurality of pixels (16) at plurality of pixel locations (17) corresponding to the marking pattern (50) which may be input by the computer user (51). Execution of the instructions may produce a marking control signal (78a) for steering the pair of mirrors (10)(11) with a steering controller (69) to direct the laser beam (2) to each of the plurality of pixels (16) at each of the corresponding pixel locations (17) on the marking plane (12) for an assigned irradiation dwell period (20) according to the marking pattern (50). In certain embodiments, execution of additional instructions may produce a marking control signal (78b) for operating a carrier position controller (70) to position a marking carriage (52). In certain embodiments the instructions may provide marking control signals (78b) for manipulating the marking carriage (52) to serially position multiple straws (61) within the travel range (53) of the laser beam (2).

Now referring primarily to FIG. 3, particular embodiments of the invention include a numerous and wide variety of polymeric members (54), particularly polymeric members (54) having thin and/or curved surfaces. Particular embodiments of the polymeric members (54) have an axial body (55) which defines an axial passage (56) communicating between a pair of body ends (57)(58) including, but not limited to, cylindrical vessels (59) defining a cylindrical passage (60) (as shown in FIG. 3). As a non-limiting example, some embodiments relate to straws (61) for containing a variety of biological materials, and in certain embodiments, cryogenically frozen biological materials such as embryos, semen, ova, sperm cells, sex-selected sperm cells (subpopulations of sperm cells selected on the basis of being X-chromosome bearing or Y-chromosome bearing), sex-selected embryos, or the like. Straws (61), as a non-limiting example, can have a length of about 133 mm or about 280 mm with an outer diameter in the range of about 0.8 mm to about 5 mm and an inner diameter in the range of about 0.7 mm to about 4.9 mm and having in a wall thickness in the range of about 0.1 mm and about 0.2 mm.

FIG. 4 illustrates a cross sectional view of the straw (61) seen in FIG. 3. The interior surface (86) and exterior surface (85) of the straw (61) can be seen defining a straw thickness (87). Some depth of the visible mark (18) can also be seen in this cross sectional view.

Table 1 provides a non-limiting list of straws (61) suitable for use with particular embodiments of the invention which can be obtained from IMV Technologies, 10, rue Clemenceau, 61300 L'Aigle, France, or other sources.

TABLE 1

| Straws | Color | Cat. No. |
|---|---|---|
| 0.5 ml | clear | 5569 |
| 0.5 ml | red | 5702 |
| 0.5 ml | green | 5568 |
| 0.5 ml | purple | 5703 |
| 0.5 ml | yellow | 5707 |
| 0.5 ml | salmon | 5715 |
| 0.5 ml | putty colored | 5711 |
| 0.5 ml | pistachio | 5746 |
| 0.5 ml | pink | 5712 |
| 0.5 ml | pastel red | 5709 |
| 0.5 ml | pastel green | 5710 |
| 0.5 ml | pastel blue | 5697 |
| 0.5 ml | pastel grey | 5698 |
| 0.5 ml | pastel yellow | 5590 |
| 0.5 ml | pastel orange | 5685 |
| 0.25 ml | clear | 5565 |
| 0.25 ml | green | 5570 |
| 0.25 ml | purple | 5573 |
| 0.25 ml | yellow | 5578 |
| 0.25 ml | pink | 5581 |
| 0.25 ml | light blue | 5680 |
| 0.25 ml | salmon | 5582 |

TABLE 1-continued

| Straws | Color | Cat. No. |
|---|---|---|
| 0.25 ml | putty colored | 5585 |
| 0.25 ml | pastel red | 5567 |
| 0.25 ml | pastel blue | 5584 |
| 0.25 ml | pastel grey | 5577 |
| 0.25 ml | pastel yellow | 5575 |
| 0.25 ml | pastel orange | 5580 |
| 0.25 ml TBS | clear | 17011 |
| 0.25 ml TBS | pastel orange | 17017 |
| 0.25 ml TBS | pastel grey | 17015 |
| 0.25 ml TBS | pastel red | 17012 |
| 0.25 ml TBS | pastel pistachio | 18888 |
| 0.25 ml TBS | salmon | 19708 |
| 0.25 ml TBS | pink | 19707 |
| 0.25 ml TBS | white | 18299 |
| 0.25 ml TBS | pastel yellow | 17016 |
| 0.25 ml TBS | pastel green | 17013 |
| 0.25 ml TBS | pistachio | 19709 |
| 0.25 ml TBS | pastel blue | 17014 |
| 0.25 ml | white plug | 6937 |
| 0.25 ml | grey plug | 6939 |
| 0.25 ml | yellow plug | 6942 |
| 0.25 ml | red plug | 6941 |
| 0.25 ml | blue plug | 6940 |
| 0.25 ml | green plug | 6938 |

Embodiments of the polymeric members (54) including conventional artificial insemination straws (61) are formed from polyvinyl chloride ("PVC") and polyethylene terephthalate ("PETG"). Additives such as carbon black, graphite, calcium silicates, zirconium silicates, zeolite, mica, kaolin, talc cordierite, and colorants such as organic pigments, inorganic pigments, photochromic dyes, or polymer-compatible organic dyes can be dispersed throughout the polymeric matrix (65) of the polymeric members (54). These polymers have been shown to be impermeable to a wide range of biological materials including impermeability to hepatitis B and HIV-1 virus and other viruses, or the like, even when the straws containing the biological materials are cryogenically frozen. Benifla, Jean-Louis et al., "*Safety of cryopreservation straws for human gametes or embryos: a preliminary study with human immunodeficiency virus 1*", Human Reproduction, Vol 15, No. 10, 2186-2189 (October 2000).

However, as above described, polymeric members (54) have not been laser marked previously because attempts to generate a visible mark (18) on the marking plane (12) of polymeric members (54), including straws (61) such as those listed in Table 1, results in either no visible mark (18) or in a visible mark (18) which causes permeability and transfer of the contained biological materials or results in deformation of polymeric member (54) to an extent which precludes the use of automated or manual downstream processes to fill the polymeric members (54) with biological materials, store, or utilize the polymeric member (54) for the intended purpose.

Figure 5:
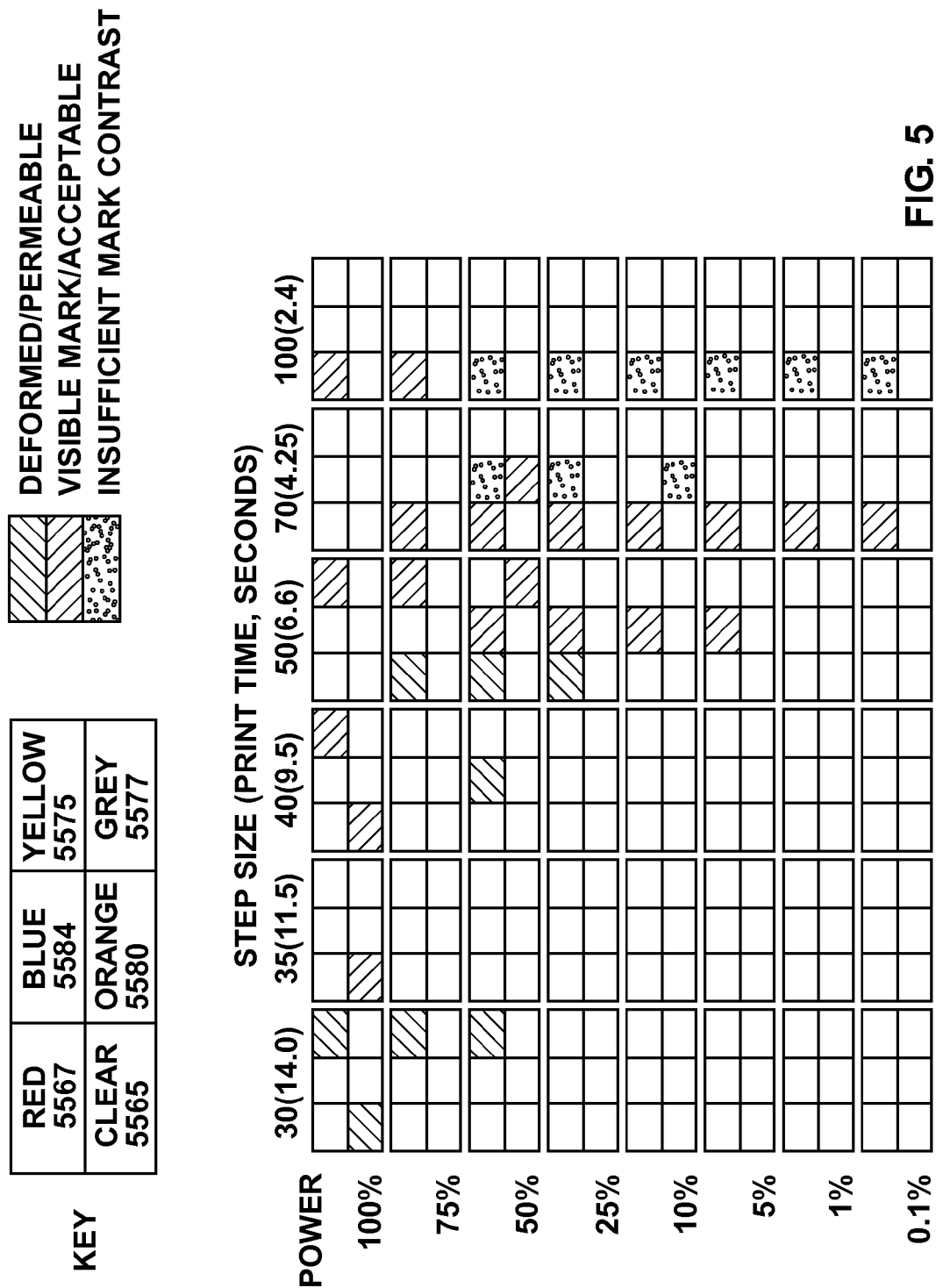
FIG. 5 illustrates the results of trials in which a plurality of polymeric members are each laser marked according to certain embodiments described herein.

FIG. 5 provides a tabular summary of the results obtained in trials in which a laser beam (2) was made incident upon a marking plane (12) of certain embodiments of a polymeric member (54) formed from a PVC polymer to provide a length of about 133 mm with an outer diameter of about 4 mm and an inner diameter in the range of about 3.8 mm resulting in a wall thickness of about 0.1 mm. Each trial was performed using a laser source (1) which included a vanadate (Nd:YVO4) laser crystal (7) which absorbs laser light (4) at 808 nanometers ("nm") from a laser diode (3) to produce a continuous waveform laser light (4) at a wavelength of 1064 nm, frequency-doubled to produce a laser beam (2) having a wavelength of 532 nm. The laser beam (2) was switched using a Q-switch (8) to generate laser beam pulses (9) having a frequency of 10 kHz. The boundary (14) of the laser beam (2) incident upon the marking plane (12) of each polymeric member (54) was fixed to establish a laser beam spot (13) having a diameter of about 40 μm. The fluence (62) of each of the plurality of laser beam pulses (9) was controlled by adjusting the amperage (48) of the current delivered to the laser diode (3) to achieve a range of power adjustable between 0.1% and 100% of about 2 W. The step size (88), or distance between each of a plurality of pixel locations (16), was controlled by the marking module (37) of the computer (21) to establish a range of distance between any two of a plurality of pixels (17) (also referred to as "step size") within a range of about 30 μm and about 100 μm. The plurality of pixel locations (16) established by the marking module (37) of the computer (21) matched a marking pattern (50) constant between trials. The laser beam (2) was centered incident upon each of the plurality of pixels (16) included in the marking pattern (50) for a irradiation dwell period (20) controlled by the marking module (37) to achieve a write time (63) for the marking pattern (50) in a range of about 2.4 seconds and about 14 seconds.

Now referring primarily to FIG. 5, in accordance with the procedure above-described seventeen individual trials were conducted on a corresponding plurality of polymeric members (54) obtained from IMV Technologies, 10, rue Clemenceau, 61300 L'Aigle, France, having catalog number 5702 (Red) (see key in FIG. 5 upper left hand corner of each data grid). Fluence (62) of laser beam pulses (9) was adjusted between 0.1% and 100% of 2 W and the step size was adjusted between about 50 μm and about 100 μm as above described to generate various laser marking conditions. All other laser marking parameters were fixed at constant values between trials. As can be understood from the results of the trials set out in FIG. 5, and consistent with conventional wisdom indicating that polymeric members (54) cannot be laser marked, certain of the marking conditions either did not produce a visible mark (18) or generated a visible mark (18) but resulted in permeability or deformation of the polymeric members (54) which made each of these polymeric members (54) unsuitable for the intended use of containing biological materials. Unexpectedly, in a narrow range of conditions show by FIG. 5, it was possible to laser mark (without creating permeability or deformation of the polymeric member (54)) this particular embodiment of a polymeric member (54) by utilizing a step size of 70 μm or 100 μm and respectively a power of between about 0.1% and 75% of 2 W or 100% of 2 W. It is interesting to note that at a step size of 100 μm no visible marking (18) occurred at less than 75% of 2 W power, while at a step size of 70 μm it was possible to visibly mark (18) each polymeric member (54) within the wide range of power between about 0.1% and about 75% of 2 W.

Again referring primarily to FIG. 5, in accordance with the procedure above-described six individual trials were conducted on a corresponding plurality of polymeric members (54) obtained from IMV Technologies, 10, rue Clemenceau, 61300 L'Aigle, France, having catalog number 5584 (Blue) (see key in FIG. 5 upper middle of each data grid). Fluence (62) of laser beam pulses (9) was adjusted between 5% and 100% of 2 W and the step size was adjusted between about 40 μm and about 70 μm as above described to generate various laser marking conditions. All other parameters were fixed at constant values between trials. As can be understood from the results of the trials set out in FIG. 5, and consistent with conventional wisdom certain of the marking conditions either did not produce a visible mark (18) or generated a visible mark (18) but resulted in permeability or deformation of the polymeric members (54) which made each of these polymeric members (54) unsuitable for the intended use of containing biological materials. Again unexpectedly, in a narrow range of conditions, it was possible to laser mark this particular embodiment of a polymeric member (54) by utilizing a step size of 50 μm and a power of between about 5% and 50% of 2 W. A lack of predictability is evidenced by the step size and power useful in laser marking polymeric members (54) catalog number 5567 (Red) which failed to produce visible marks (18) on polymeric members (54) catalog number 5584 (Blue).

The remainder of the trials were performed in accordance with the procedure above-described on a variety of different polymeric members (54) obtained from IMV Technologies, 10, rue Clemenceau, 61300 L'Aigle, France, having catalog numbers 5565 (Clear), 5580 (Orange), 5575 (Yellow), and 5577 (Grey) (see the Key in FIG. 5). As to each particular embodiment of the polymeric member (54) the trial conditions which produced a visible mark (18) without resulting in permeability or deformation of the polymeric member substantially varied; however, unexpectedly as to each embodiment of polymeric member a narrow range of trial conditions allowed the polymeric member (54) to be visibly marked (18) by incidence of the laser beam (2) without resulting in permeability or deformation of the polymeric member.

The results of the 37 trials evidence that the conditions under which a laser beam (2) can induce a visible mark (18) on the marking plane (12) of a polymeric member (54) can vary substantially and unpredictably between a plurality of polymeric members (54) differentiated by dispersed colorant (64) within the corresponding polymeric matrices (65). None-the-less, as to each embodiment of polymeric member (54) a narrow set of laser marking conditions can be established which allow visible marking (18) without resulting in permeability or deformation of each type of polymeric member (54).

One aspect relates to the desire to laser marked straws (61) quickly while maintaining straw integrity for holding biological materials. The described systems and methods relate to adjusting the irradiation dwell period (20) and fluence (62) based on the characteristics of the straws (61) in order to reduce damage to straws (61) while producing visible marks (18). Additionally, laser fluence (62), step size (88) and/or irradiation dwell period (20) can further be reduced and laser marking can further be improved by coordinating or matching additives (71), such as colorants (64) having electromagnetic radiation absorbance properties with lasers beams (2) of particular wavelengths. FIG. 5 demonstrates the ability to reduce both laser power and the time required by utilizing complimentary colorants (64) and laser sources (1). Specifically, laser sources (1) may have laser beam (2) wavelengths matched to certain electromagnetic radiation absorbance properties of the polymeric members (54) being marked. The process of marking with a laser, such as etching, results in both localized charring type "photo damage" and heat dissipation through a region which can result in warping and loss of integrity. The 37 trials demonstrated that it may be desirable to coordinate marking materials and laser sources in a manner that tends to produce charring type of photo damage, as opposed to producing heat transference which may warp a straw.

Figure 6:
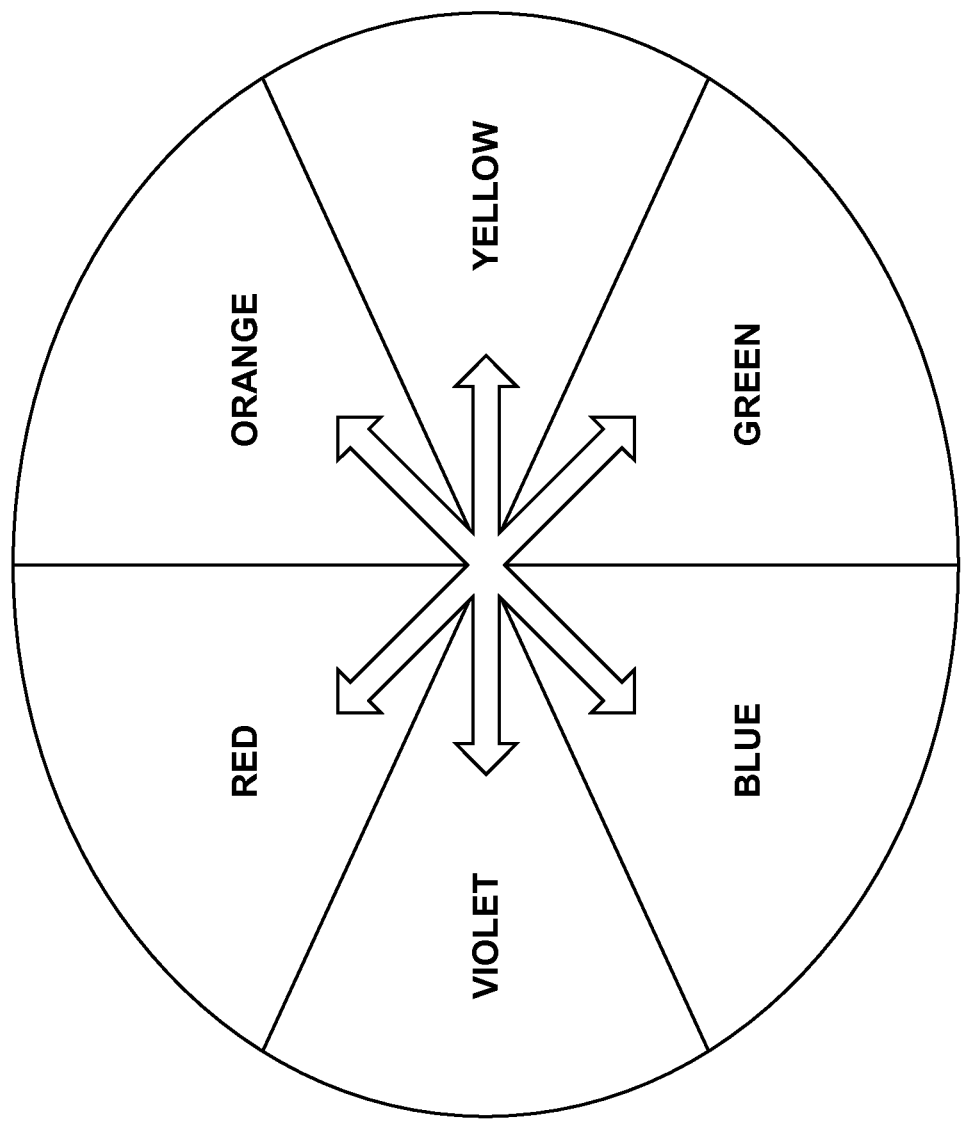
FIG. 6 illustrates a color wheel indicating complimentary primary and secondary colors.

The results of the 37 trials indicate step size can be improved, reducing straw marking times, and laser fluence (62) can be reduced, generally reducing straw (61) damage and warping, by coordinating or matching an additive (71), such as a colorant (64), or dye, having electromagnetic radiation absorbance properties to the laser source (1). While some interplay exists between step size (88) and laser fluence (62), there is level of unpredictability in producing visible marks (18) on thin polymeric members (54). However, a benefit can be seen for matching colorants (64) with electromagnetic radiation absorbance properties that peak at or near the wavelength of the laser source (1). Examples of desirable electromagnetic radiation absorbance properties can be a maximum electromagnetic radiation absorbance wavelength or a local maximum electromagnetic radiation absorbance wavelength. Colorants (64), or dyes, which are visible complimentary colors to the color of the laser wavelength may exhibit good absorbance properties at the wavelength of the laser source. In FIG. 6 a color wheel illustrates the primary and secondary colors and related complimentary colors.

FIG. 5 demonstrates improved straw (61) marking when straw (61) colors are selected corresponding to, or approximately matched to, the wavelength of the laser source (1). The 37 trials demonstrate absorption of such matched lasers and straws (61) provide for the desired localized type of "photodamge" characterized by shallow divots and charring for improved contrast, whereas those laser emissions which are not so matched result in less localized affects resulting in deeper divots, as well as, more heat transferred to the surrounding area, and a greater tendency to warp the straws (61). Additionally, more power might be required to achieve the desired charring "photodamage," in unmatched straws and lasers compounding the tendency to warp the straws (61).

In particular, FIG. 5 illustrates results with good markings at low laser powers and at faster times for a 532 nm wavelength ("green") laser on red straws. Red and green can be considered complimentary colors, as a red dye exhibits good absorbance for light in the green range of the visible spectrum. Specifically, the red straw could be marked 2.4 seconds utilizing 75% 2 W power or with as little as 10 mW in 4.25 seconds. Even at 25% power the laser produced enough heat to warp the red straw in 6.6 seconds. In contrast, the yellow dye was not able to produce visible marks at 50 mW in 4.25 seconds. The orange straw, which would have electromagnetic radiation absorbance characteristics close to that of a red straw, produced visible marks at 50% power in 4.5 seconds. In further contrast, the clear straw did not warp until marking for 14 seconds.

Figure 7:
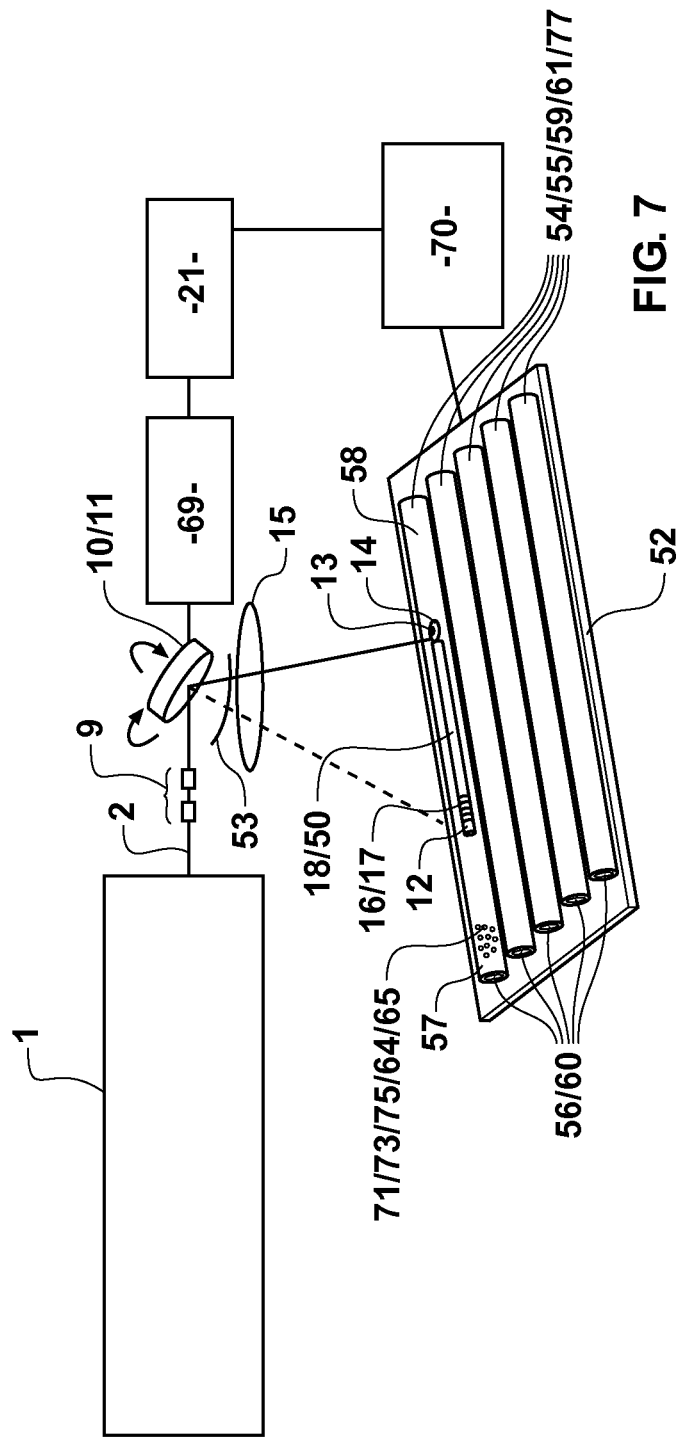
FIG. 7 illustrates a diagram relating to embodiments described herein.

Various embodiments described herein relate to methods emulating the behavior of the red straws subjected to the 532 nm (green) laser. With Reference to FIG. 7, one such method can include the step of obtaining a polymeric member (54), where the polymeric member (54) is formed from a polymeric matrix (65) including an additive with electromagnetic radiation absorbance properties. The additive can be a dye or colorant (64), which can have good electromagnetic radiation absorbance at certain wavelengths and even a maximum electromagnetic radiation absorbance wavelength. The electromagnetic radiation absorbance properties of the additive (71) can be matched with the wavelength of the laser source (1), so the colorant (64) tends to absorb the laser energy well. This concept can be referred to as "impedance matching."

A marking plane (12) can be defined on the surface of the polymeric member (54). A laser beam (2) can be emitted from the laser source (1) and directed incident upon the marking plane (12) on the surface of the polymeric member (54). The matched laser beam (2) can then be optically focused incident upon the marking plane (12) on the surface of the polymeric member (54) to establish a laser beam spot (13) having a fixed dimensional boundary (14). Finally, the polymeric member (54) can be visibly marked on the marking plane (12).

Matching the laser source (1) with electromagnetic radiation absorbance properties of the additive (71) may include substantially matching the wavelength of the laser beam (2) with the maximum absorbance wavelength of the colorant (64), or dye, or with wavelengths at which the colorant (64) exhibits good electromagnetic radiation absorbance (such as a local maximum). This matching may occur within the visible light spectrum of about 400 nm-700 nm or in the ultra violet frequency range 250 nm-400 nm. As one example, the matching of the maximum absorbance wavelength of the colorant (64) and the laser beam (2) wavelength may occur within about 60 nm, or within about 40 nm. As another example, the matching of the wavelengths may broadly be considered selecting both laser beam (2) wavelengths and colorants (64) with maximum absorbance wavelengths characterized within the same family of primary or secondary colors. With reference to the visible color of the colorants (64), this matching may also be considered as selecting lasers characterized as primary or secondary colors which are complimentary to the visible colors of the colorants (64). Similarly, straws (61) may be selected for including dyes or colorants (64) which are complimentary in color to the wavelength of the laser source.

As another specific non-limiting example, the polymeric member (54) may be doped with an additive (71) that absorbs light well in the ultra violet frequency range. The polymeric member (54) may then be marked with a laser source (1) operating at a wavelength in ultra violet range, such 150 mW laser available from Vanguard operating at 355 nm, regardless of the color of the polymeric member (54). One example of an additive (71) is a colorant (64) which absorbs light in the ultra violet frequency range and may include photochromic dyes (73). Photochromic dyes (73) may be considered dyes which exhibit different light absorption or emission spectra in response to certain conditions. The exposure of the photochromic dye (73) to ultraviolet light, or natural light with an ultraviolet component, may be one such condition which varies the absorption or emission spectra of the dye (73). Photochromic dyes (73) may comprise dyes from the spironaphthoxazines and naphthopyrans families, which undergo physical changes to their chemical structure in response to particular frequencies of electromagnetic radiation including light in the ultraviolet frequency range and are generally characterized as shifting from transparent to a selected color, when activated. Photochromic dyes (73) of this nature are commercially available as Reversacol™ dyes from James Robinson Ltd., Huddersfield, United Kingdom, and are described in more detail in U.S. Pat. Nos. 5,559,231 and 6,303,673, each of which are incorporated herein by reference. These dyes may be incorporated into clear straws or straws with any basal color having a basal dye (75). As compared to the 532 nm "green laser", the 355 nm "UV" laser provides higher energy photons which are delivered at a greater frequency. The combination of higher energy photons and increased beam frequency may increase the resolution of the laser etching and reduce the time required to make a visible mark.

Additionally, 0.25 ml straws (61) may be constructed from a Polyethylene terephthalate PETG for its durable qualities. However, PETG is sensitive to ultra violet light and becomes brittle and opaque when exposed to sunlight for a long period. For this same reason, an ultra violet laser is expected to mark on PETG straws (61) with a high contrast. An ultra violet laser source (1) may be used for etching PETG straws (61) at increased speeds with reduced fluence (62). The use of ultra violet laser source (1) would additionally provide the benefit of requiring a substantially uniform fluence (62) and irradiation dwell period (20) as compared to the 532 nm laser regardless of straw basal color because the basal colors would not demonstrate differences in the absorbance of the ultra violet laser. The addition of a photochromic dye (73) may further improve the ability to mark on PETG straws (61) with an ultra violet laser source (1), by further reducing the fluence (62) required to make a visible mark.

As one example, the step of matching a colorant (64) with a laser source (1) may begin by selecting a commercially available laser such as a 266 nm, 355 nm 532 nm or 1064 nm Vanguard lasers at 150 mW or at 350 mW, available from Spectra Physics. The polymeric members (54), such as straws (61), may then be selected or produced having properties which tend to absorb the wavelength of visible or ultra violet light produced by the selected laser source (1). A colorant (64) may be dispersed in the polymeric matrix (65) of the polymeric member (54) for this purpose. As one example, polymeric members (54) may be selected having photochromic dyes (73) for use with the 266 nm and 355 nm lasers. As another example, polymeric members (54), which absorb green light, such as red polymeric members (54), may be paired with the lasers sources (1) operating a wavelengths characterized as green, such as 532 nm. Similarly, lasers sources (1) throughout the ultra violet and visible light spectrum may be selected and matched with complimentary polymeric members (54). Table 2 illustrates commercially available lasers sources (1) at common operations frequencies, although tunable lasers are also available which may achieve a range of wavelengths. Each listed laser servers only as an example and many other lasers and laser wavelengths are envisioned within the scope of this invention. In Table 2 the laser color is a generalization referencing either the primary, or secondary color to which the wavelength is the closest.

TABLE 2

| Laser | Wavelength (nm) | Laser Color | Complimentary Dye Color |
|---|---|---|---|
| Vanguard (nd:YAG)[1] | 266 nm | UV | Photochromic dye[3] |
| Vanguard (nd:YAG)[1] | 355 nm | UV | Photochromic dye[3] |
| 85/95 Argon[2] | 458 nm | Blue | Orange |
| 85/95 Argon[2] | 488 nm | Blue | Orange |
| Vanguard (nd:YAG)[1] | 532 nm | Green | Red |
| 85/95 Argon[2] | 514 nm | Green | Red |
| Copper Vapor Laser | 578 | Yellow | Violet |
| Helium-Neon Laser[1] | 633 nm | Red | Green |
| 85/95 Krypton[2] | 676 | Red | Green |
| Vanguard (nd:YAG)1 | 1064 nm | Infrared | — |

[1]available from Spectra Physics
[2]available from Lexel Lasers
[3]available from James Robinson Ltd.

In another embodiment, the polymeric members (54) may be constructed from a polymeric matrix (65) with a colorant (64), or dye, dispersed for achieving a desired color. The laser source (1) may then be matched as complimentary to the color of the polymeric member (54).

In one embodiment, the fluence (62) of the laser beam (2) can be adjusted to produce a visible mark (18) on the matched polymeric member (77). The fluence (62) can be minimized in order to reduce warping of the matched polymeric member (77) while still producing a visible mark (18). The fluence (62) may be adjusted by adjusting the irradiation dwell period (20) may be adjusted to speed up marking polymeric members (54). The output energy of the laser source (1) may also be reduced to adjust the fluence (62) of the laser beam (2).

Figure 8:
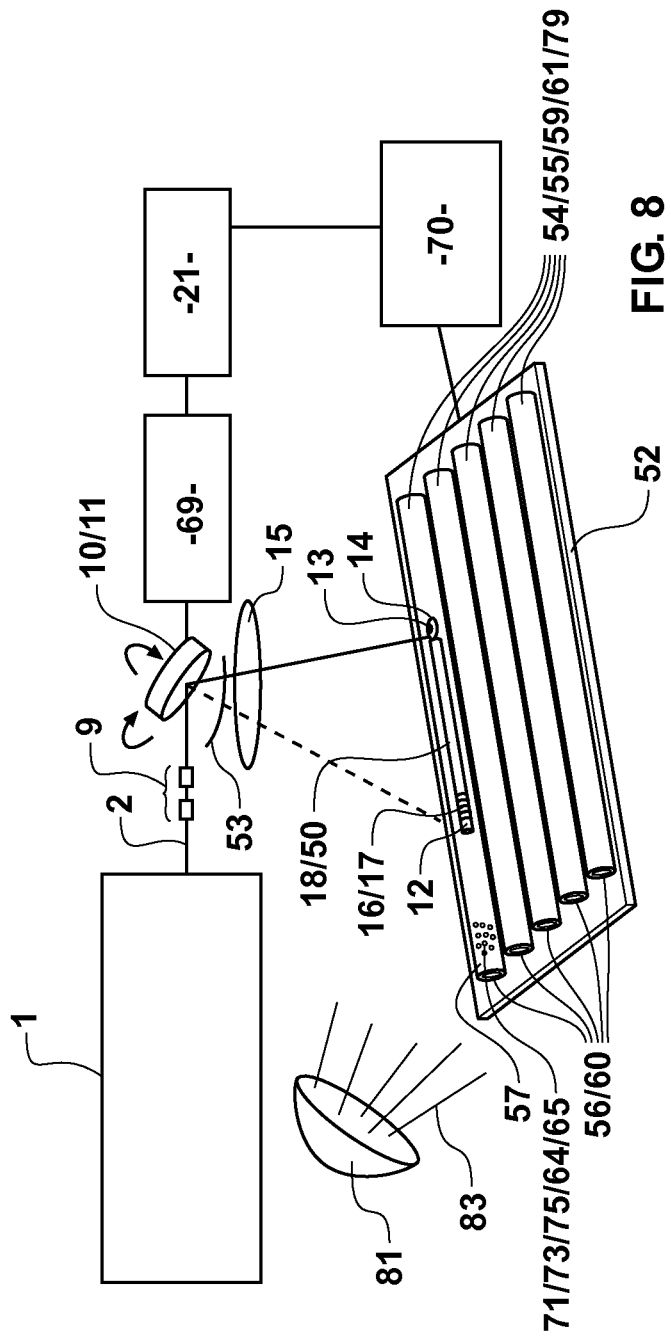
FIG. 8 illustrates a diagram relating to embodiments described herein.

With reference to FIG. 8, another method may include obtaining a polymeric member (54) formed from a polymeric matrix (65) including a photochromic dye (73) which can be transitioned from an inactive state to an activated state. The photochromic dye (73) may remain relatively colorless in the inactive state and can have a selected visible color in the activated state. The photochromic dye (73) can be selected and matched such that the visible color in the active state is complimentary to the laser source (1) used for marking. Such dyes tend to have good absorbance in at least some portion of the ultra violet frequency range, but may also have good absorbance, or a local maximum absorbance wavelength, which can be matched with the wavelength of the laser source (1).

The method may continue with the activation of the photochromic dye (73). Once activated, the photochromic dye (73) may either transition from a transparent polymeric member (54) to a preselected color, or may have a combined effect with a basal dye (75) in the polymeric matrix (65) and alter the existing color of a polymeric member (54). In either event, when the visible color of the activated photochromic dye (73) is complementary to the wavelength of the laser source (1), the activated polymeric member (79) may demonstrate an improved absorbance for the laser source (1) resulting in improved marking.

The method can continue with defining a marking plane (12) on the surface of the polymeric member (54) and matching a laser source (1) with an electromagnetic radiation absorbance property of the photochromic dye (73) in the activate state and activating the photochromic dye (73) within the polymeric member (54) defining a marking period. The period during which the photochromic dye (73) is activated can define a marking period and may be achieved with a ultra violet lamp, an arc lamp, or another source of electromagnetic radiation (81) producing activation energy (83) depending upon the activation properties of the photochromic dye (73).

The laser source (1) can emit a laser beam (2) directed incident upon the marking plane (12) on the surface of the polymeric member (54) during the marking period. The laser beam (2) can be optically focused incident upon the marking plane (12) on the surface of the polymeric member (54) to establish a laser beam spot (13) having a fixed dimensional boundary resulting in visibly marking the polymeric member (54) on the marking plane (12) on the surface of the polymeric member (54) during the marking period.

The laser source (1) may be selected with a wavelength in the visible light frequency range of about 400 nm to about 700 nm and may be matched with the maximum absorption wavelength of the photochromic dye (73) in the activated state within about 60 nm, or within about 40 nm Table 3 below illustrates the Reversacol™ product line of photochromic dyes and their maximum absorbance wavelengths in the activated state.

TABLE 3

| Name | λ max (nm) - activated |
|---|---|
| Corn Yellow | 455 |
| Rush Yellow | 430 |
| Sunflower | 445 |
| Solar Yellow | 430 |
| Flame | 475 |
| Poppy | 500 |
| Cardinal | 505 |
| Cherry | 520 |
| Berry Red | 490 |
| Claret | 545 |
| Ruby | 490 |
| Amethyst | 560 |
| Plum Red | 555 |
| Palatinate Purple | 595 |

TABLE 3-continued

| Name | λ max (nm) - activated |
|---|---|
| Storm Purple | 585 |
| Lilac | 540 |
| Oxford Blue | 570 |
| Velvet Blue | 570 |
| Sea Green | 635 |
| Aqua Green | 610 |
| Heather | 476, 546 |
| Misty Grey | 485, 570 |
| Midnight Grey | 485, 570 |
| Graphite | 485, 585 |

The photochromic dye (73) may be characterized as having two local maxima in the light absorption spectra. The first local maxima may correspond to the ultra violet frequency range, indicating the energy which is absorbed in the reaction that causes a color shift. The second local maximum may be characteristic of the activated visible color. A photochromic dye may be matched directly to a laser operating in the ultra violet frequency range, or may have an activated state matched to a particular laser. In the activated state such a photochromic dye would be tinted with a color which is complementary to the color of the laser source (1). Examples, as demonstrated in FIG. 6, include: a red activated photochromic dye and a green laser; a blue activated photochromic dye and an orange laser; a yellow activated photochromic dye and a violet laser; a green activated photochromic dye and a red laser; an orange activated photochromic die and a blue laser; and a violet activated photochromic dye and a yellow laser.

As one non-limiting example, a straw containing any basal colorant may additionally be doped with the photochromatic colorant Plum Red available under the trade name Reversacol™ from James Robinson (UK). The photochromatic dye may then be activated with an ultra violet lamp or other source of ultra violet light. Once activated, a 532 nm "green" laser, such as a Vangaurd 532, may be used to produce a visible mark on the straw. A straw doped with a photochromic dye matched to the marking laser may be printed quicker and with less power than straws having unmatched basal dyes without photochromic additives.

In one embodiment, the step of activation may be performed by the marking laser (1). As a non-limiting example, a green laser used for marking may interact with the polymeric member (54) to produce frequency doubled wavelengths of light. In such an embodiment, a green laser operating at 532 nm may be frequency doubled to produce some light at a near ultraviolet wavelength 266 nm. The number of photons frequency doubled in this manner may be a small fraction of the total photons, but may be sufficient to activate a photochromic dye (73) within the polymeric member (54). In such an embodiment, a green laser may both mark a polymeric member (54) and to activate the photochromic dye (73) in the polymeric member (54).

Certain embodiments also relate to the apparatus of a polymeric member (54) seen in FIGS. 7 and 8 for storing and transporting biological material. The polymeric member (54) may include a axial body (55) which defines an axial passage (56) between a pair of body ends (57)(58), and in particular a cylindrical body (59) defining a cylindrical passage (60). The cylindrical body (60) may have an exterior surface (85) and may be formed from a polymeric matrix (65) including a photochromic dye (73). The photochromic dye (73) may be selected to change the color of the polymeric member (54) in visible light or under ultra violet light. In one embodiment, the polymeric member (54) may be activated by ultra violet light, and may also serve to protect the biological materials from ultra violet exposure. The apparatus may further include a plug for sealing the substantially tubular polymeric member.

The polymeric member may comprise a straw (61) for storing or transporting biological materials including those selected from: an amount of semen, an ova, ovum, an enucleated cell, a plurality of sperm cells, an embryo, a plurality of sex-selected sperm cells, a sex-selected embryo, a pathogen, a bacteria, and a virus. The straw (61) may have a thickness between about 0.1 mm and 0.2 mm and may be constructed from a polyvinyl chloride or a polyethylene terephthalate. In some embodiments materials may be marked having thicknesses less than 0.5 mm.

Figure 9:
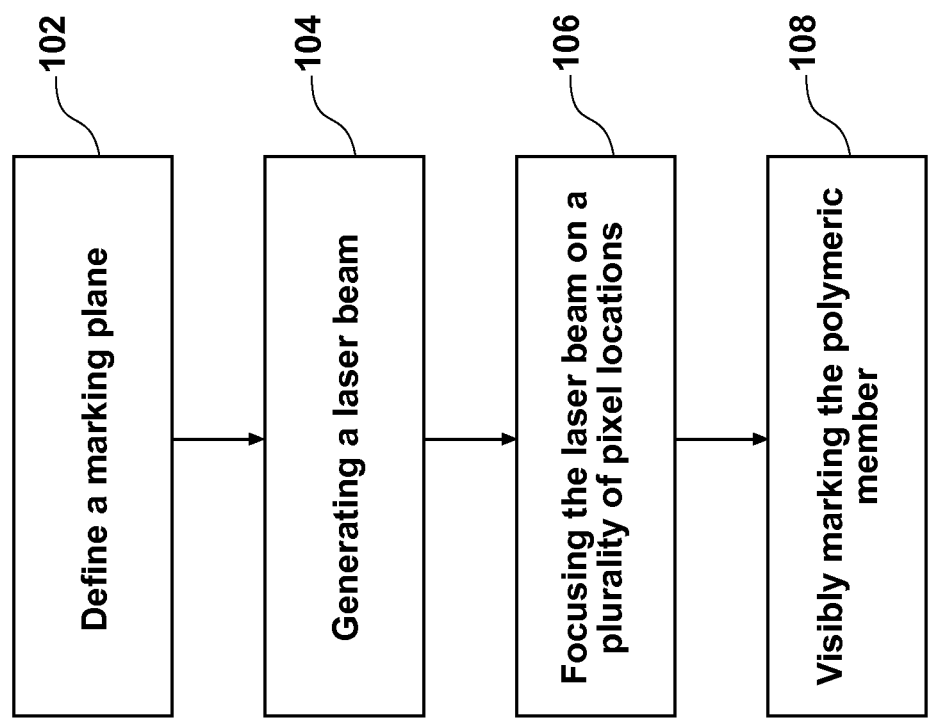
FIG. 9 illustrates a block diagram relating to methods described herein.

Referring to FIG. 9, a general method is illustrated (100). The method may begin at step (102) with defining a marking plane (12). The marking plane (12) may be defined on a thin curved surface, such as a polymeric member (54) having an axial body (55) defining an axial passage (56) communicating between a pair of body ends (57/58). As one example, the marking plane (12) may be the exterior surface of a cylindrical vessel (59) and as another example the marking plane (12) may be the exterior surface of a 0.25 ml or 0.5 ml straw (61). The step of defining a marking plane (12) may be executed in the form of processing computer instructions described in FIG. 2 and may be done alone, or in combination with user input (51). Using a computer (21) like the one described in with respect to FIGS. 2 and 3, multiple marking planes may be defined on plurality of straws for sequential marking.

At step (104) a laser beam (2) is generated, such as by any of the lasers sources (1) previously described. In some embodiments, it may be desirable to select a laser source (1) with particular characteristics to facilitate producing visible marks on thin, curved surfaces. As one example, a wavelength, or other operational characteristic, of the laser source (1) may be coordinated with a color of the straws (61) being marked. In such an embodiment, the polymeric member (54) may contain an additive (71), such as a colorant (64), or dye, which may be doped into the polymeric matrix (65) of the polymeric member (54). The colorant (64) may have electromagnetic radiation absorbance properties, such as local or absolute maxima in the absorption spectra. The local or absolute maxima of the absorption spectra may be in the ultra violet or visible light wavelength ranges. For example, the local or absolute maxima of the absorbance spectra may be in the range of about 250-400 nm, or in the range of about 400 nm-700 nm. The local or absolute maxima of the absorbance spectra may also be matched or loosely matched to particular wavelengths of specified lasers, such as about 266 nm, 355 nm, 435 nm, 460 nm, 532 nm, 555 nm, or 570 nm. In one embodiment, the laser source (1) may comprise a laser source (1) operating at a wavelength of 355 nm and the colorant (64) having a local maximum in the absorbance spectra between about 300 nm and 380 nm.

As another example, the fluence (62), irradiation dwell period (20), and/or step size (88) may be adjusted based on the material being marked or based on the color of the curved surface. Conversely, it may be desirable to select straw colors based upon the laser source (1) to be used. In some embodiments, straws (61) may be doped with photochromatic dyes (73). Alternatively, only the portions of the straws (61) comprising the marking plane (12) may be doped with photochromatic dyes (73). A laser operating at the ultra violet wavelength may be used for directly marking on such straws doped with photochromatic dyes.

In another embodiment, straws (61) may be doped with a photochromatic dye providing the straws with an active state and an inactive state. An arc lamp, ultra violet light source, or other light source generally containing light at the ultra violet frequency may be used to shift straws (61) from the inactive state to an active state. Straws (61) in the active state may exhibit different color properties and different laser absorbance properties as compared to their inactive state.

At step (106) the laser beam may be focused on a plurality of pixel locations on the marking plane or multiple marking planes. The step size and irradiation dwell period may be adjusted in a computer (21) based upon the surface to be marked, the material to be marked, the color of the material to be marked, or the activated color of the material to be marked when activated. Such adjustments may be made for the purpose of visibly marking a surface without causing the deformation of the member and without the surface becoming permeable.

At step (108) a visible mark (18) may be produced on the surface of the polymeric member (54). The polymeric member (54) may remain undeformed and impermeable after such marking.

As can be easily understood from the foregoing, the basic concepts of the present invention may be embodied in a variety of ways. The invention involves numerous and varied embodiments of a straw laser marker including the best mode and methods of using such embodiments of the straw laser marker to induce visible marks on a marking plane of a wide and numerous variety of polymeric members, cylindrical vessels and straws.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of an "laser marker" should be understood to encompass disclosure of the act of laser marking"—whether explicitly discussed or not—and, conversely, were there effectively disclosure of the act of "laser marking", such a disclosure should be understood to encompass disclosure of an "laser marker" and even a "means for laser marking." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

Thus, the applicant(s) should be understood to claim at least: i) each of the polymeric members, or straws, disclosed and described, ii) each of the straw laser marker methods herein disclosed and described, iii) the related systems and devices disclosed and described, iv) similar, equivalent, and even implicit variations of each of these devices and methods, v) those alternative embodiments which accomplish each of the functions shown, disclosed, or described, vi) those alternative designs and methods which accomplish each of the functions shown as are implicit to accomplish that which is disclosed and described, vii) each feature, component, and step shown as separate and independent inventions, viii) the applications enhanced by the various systems or components disclosed, ix) the resulting products produced by such systems or components, x) methods and apparatuses substantially as described hereinbefore and with reference to any of the accompanying examples, xi) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A straw comprising:
   an axial body defining an axial passage between a pair of body ends, the axial body comprising a polymeric matrix and having an exterior surface, an interior surface and a thickness between the exterior surface and the interior surface, wherein the thickness between the exterior surface and the interior surface is between about 0.1 mm and about 0.2 mm;
   a photochromic dye having a maximum electromagnetic radiation absorbance wavelength or a local maximum electromagnetic radiation absorbance wavelength; and
   a laser etched mark on the exterior surface of the axial body, the laser etched mark being made with a laser having a wavelength matched to the maximum electromagnetic radiation absorbance wavelength or the local maximum electromagnetic radiation absorbance wavelength of the photochromic dye in a straw, wherein the laser etched mark modifies the surface depth and color of the exterior surface of the straw and wherein the straw remains unwarped and impermeable.

2. The straw as described in claim 1, wherein the straw contains a biological material selected from the group consisting of: an amount of semen, an ova, ovum, an enucleated cell, a plurality of sperm cells, an embryo, a plurality of sex-selected sperm cells, a sex-selected embryo, a pathogen, a bacteria, and a virus.

3. A straw comprising:
   a. an axial body defining an axial passage between a pair of body ends, the axial body having an exterior surface and being formed from a polymeric matrix including a photochromic dye;
   b. the photochromic dye selected to change the color in visible light and/or ultraviolet light, the photochromic dye having a maximum electromagnetic radiation absorbance wavelength or a local maximum electromagnetic radiation absorbance wavelength; and
   c. a laser etched mark on the exterior surface of the axial body, wherein the laser etched mark modifies the surface depth and color of the exterior surface of the straw and wherein the polymeric member remains unwarped and impermeable, and wherein the wavelength of a laser used to produce the laser etched mark is matched to the maximum electromagnetic radiation absorbance wavelength or local maximum electromagnetic radiation absorbance wavelength of the photochromic dye.

4. The straw as described in claim 3 wherein the straw contains a biological material selected from the group consisting of: an amount of semen, an ova, ovum, an enucleated cell, a plurality of sperm cells, an embryo, a plurality of sex-selected sperm cells, a sex-selected embryo, a pathogen, a bacteria, and a virus.

5. The straw described in claim 3 wherein the straw has a wall thickness between about 0.1 mm and 0.2 mm.

6. The straw described in claim 3 wherein the photochromic dye has an activated state and an inactivated state, and wherein light in the visible or ultra violet spectra activate the photochromic dye and change the color of the straw.

7. The straw described in claim 3 wherein the polymeric matrix of the polymeric member is selected from the group consisting of: a polyvinyl chloride and a polyethylene terephthalate.

8. The straw described in claim 3 wherein the photochromic dye provides protection for materials within the polymeric member which are sensitive to ultra violet light.

9. The straw described in claim 3, wherein the photochromic dye has an activated state and an inactivated state.

10. The straw described in claim 9, wherein the maximum electromagnetic radiation absorbance wavelength or a local maximum electromagnetic radiation absorbance wavelength of the photochromic dye comprises the maximum electromagnetic radiation absorbance wavelength or a local maximum electromagnetic radiation absorbance wavelength of the photochromic dye in the activated state.

* * * * *